United States Patent [19]

Ascione et al.

[11] Patent Number: 5,849,308
[45] Date of Patent: *Dec. 15, 1998

[54] METHOD OF PROVIDING SURFACTANT PROPERTIES TO A COSMETIC OR PHARMACEUTICAL COMPOSITION USING ALKYL N-(HYDROXYALKYL) CARBAMATES

[75] Inventors: Jean-Marc Ascione, Paris; Eric Bollens, Nogent Sue Seine; Claude Mahieu, Paris; Michel Philippe, Wissous; Isabelle Rollat-Corvol, Paris, all of France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 535,962

[22] Filed: Sep. 28, 1995

[30] Foreign Application Priority Data

Sep. 29, 1994 [FR] France .................................. 94 11665

[51] Int. Cl.$^6$ ...................................................... A61K 47/30
[52] U.S. Cl. ..................... 424/401; 424/70.1; 424/70.19; 424/70.31; 514/788
[58] Field of Search ................................... 424/401, 70.1, 424/70.19, 70.31; 514/788

[56] References Cited

U.S. PATENT DOCUMENTS

| 384,146 | 2/1888 | Mahieu et al. . |
| 2,040,997 | 5/1936 | Johnson . |
| 2,808,402 | 10/1957 | Boettner . |
| 4,382,765 | 5/1983 | Möller et al. . |
| 5,149,860 | 9/1992 | Zysman et al. . |
| 5,198,470 | 3/1993 | Zysman et al. . |
| 5,230,890 | 7/1993 | Phillippe et al. . |
| 5,354,510 | 10/1994 | Vanlerberghe et al. . |

FOREIGN PATENT DOCUMENTS

| A-543132 | 9/1959 | Belgium . |
| A-0408448 | 1/1991 | European Pat. Off. . |
| A-0420722 | 4/1991 | European Pat. Off. . |
| A-0450527 | 10/1991 | European Pat. Off. . |
| A-0577506 | 1/1994 | European Pat. Off. . |
| A-2379283 | 9/1978 | France . |
| A-2703993 | 10/1994 | France . |

OTHER PUBLICATIONS

Derwent of FR–A–2703993, 1994.

*Primary Examiner*—Rebecca Cook
*Attorney, Agent, or Firm*—Finnegan, Henderson, Farabow, Garrett & Dunner, L.L.P.

[57] ABSTRACT

The use of alkyl N-(hydroxyalkyl)carbamates in a cosmetic or pharmaceutical composition provided in the form of an aqueous lotion, a gel, an emulsion, a cream, a foam or a paste.

13 Claims, No Drawings

METHOD OF PROVIDING SURFACTANT PROPERTIES TO A COSMETIC OR PHARMACEUTICAL COMPOSITION USING ALKYL N-(HYDROXYALKYL) CARBAMATES

The present invention is directed to the use of an alkyl N-(hydroxyalkyl)carbamate in a cosmetic or pharmaceutical composition.

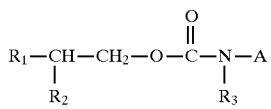

in which:
- $R_1$ represents a linear or branched, saturated or unsaturated alkyl radical having 4 to 6 carbon atoms,
- $R_2$ represents a linear or branched, saturated or unsaturated alkyl radical having 2 to 4 carbon atoms,
- $R_3$ represents a hydrogen atom or a linear or branched, saturated or unsaturated alkyl radical having 1 to 6 carbon atoms, and
- A represents a nonionic hydrophilic group, have been invented but are not believed to be prior art against the claims herein.

These compounds have excellent cosmetic properties. In particular, used in hair compositions, these compounds confer hair-styling, sleeking and coating properties to the hair and facilitate its disentanglement.

Furthermore, the compounds of formula (I) make it possible to decrease the loss of water and/or to increase the binding of water in the stratum corneum and therefore find application in the field of moisturizing compositions.

The Inventors observed, surprisingly, that the compounds according to formula (I) also had advantageous surfactant properties capable of being used in the cosmetic field.

It was more particularly observed that the compounds of formula (I) had "gentle" surfactant properties, that is to say which are substantially less irritating for the skin or the scalp than the surfactants normally used.

A subject of the present invention is therefore the use of a compound of formula (I) as a surfactant in a cosmetic or pharmaceutical composition.

Cosmetic composition is understood in the present description to mean any composition capable of being applied, inter alia, to the skin or the hair, and usually comprising a surfactant; dentibuccal compositions also being included in this definition.

The present invention also has the advantage of using compositions having a high surfactant power which is greater than that of compounds of similar structure which are known to be good surfactants. The result is the possibility of obtaining similar effects while using less surfactant compound.

Among the compounds of formula (I) as defined above, those in which A represents a radical:

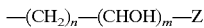

in which n is an integer equal to 0 or 1, m is an integer ranging from 0 to 4, and Z is a hydroxylated alkyl radical having from 1 to 4 carbon atoms, are preferred.

Hydroxylated alkyl radical is understood to mean a branched or linear, saturated or unsaturated alkyl radical containing 1 to 3 hydroxyl groups.

Preferably, Z may be chosen from the group comprising:

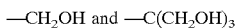

Among the compounds of formula I, there may be mentioned more preferably:
N-2-ethylhexyloxycarbonyl-N-methyl-D-glucamine,
N-2-butyloctyloxycarbonyl-N-methyl-D-glucamine,
N-2-ethylhexyloxycarbonyl-D-glucamine,
N-2-butyloctyloxycarbonyl-D-glucamine,
2-N-(2-ethylhexyloxycarbonyl)amino-2-hydroxymethyl-1,3-propanediol,
2-N-(2-butyloctyloxycarbonyl)amino-2-hydroxymethyl-1,3-propanediol,
2-N-(2-ethylhexyloxycarbonyl)amino-1-ethanol,
2-N-(2-butyloctyloxycarbonyl)amino-1-ethanol,
3-N-(2-ethylhexyloxycarbonyl)amino-1,2-propanediol, and
3-N-(2-butyloctyloxycarbonyl)amino-1,2-propanediol.

The compounds of formula (I) can be obtained by reacting, in a solvent, an amino alcohol of formula $R_3$—NH—A with a compound of formula (II):

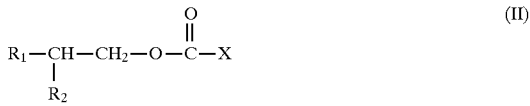

$R_1$, $R_2$, $R_3$ and A having the same meanings as those given above and X representing a halogen atom, preferably a chlorine atom, or a radical derived from an azole, preferably a radical obtained from an imidazole such as that of formula (III):

As solvent, dichloromethane, 1,2-dichloroethane, 1,1,1-trichloroethane, chloroform, acetonitrile, toluene, dioxane, tetrahydrofuran, 1,2-dimethoxyethane, cyclohexane, water or a mixture of these solvents, may preferably be used.

The reaction may preferably be performed at a temperature ranging from $-5°$ C. to $50°$ C., more preferably at a temperature less than $10°$ C.

The reaction may preferably be performed in the presence of a base. The latter may preferably be chosen from alkali or alkaline-earth metal hydroxides, sodium hydrogen carbonate, alkali metal alcoholates, alkali metal hydrides, and tertiary amines, such as pyridine or triethylamine.

The compounds of formula (I) can be used in a cosmetic or pharmaceutical composition, which may in addition preferably comprise a cosmetically acceptable vehicle such as water; organic solvents which are compatible with a cosmetic application, such as acetone, isopropanol, ethanol; fatty acid triglycerides with 6-24 carbon atoms, glycolethers, polyalkylene glycol esters and volatile silicones.

The compounds of formula (I) may preferably be present in the composition in an amount ranging from 0.1 to 10% by weight of compound relative to the total weight of the composition, and more preferably in an amount ranging from 0.5 to 5% by weight.

It was also observed that the compounds of formula (I) were highly compatible with the surfactants normally used in the cosmetic field, such as sodiumlauryl sulphate and sodiumlauryl ether sulphate. It is thus possible to reduce the irritating character for the skin of customary surfactants by combining them with one of the compounds of formula (I).

It is, for example, possible to use, as a surfactant system, a mixture comprising sodiumlauryl sulphate and N-2-ethylhexyloxycarbonyl-N-methyl-D-glucamine, preferably in a 1/1 ratio, or alternatively in proportions in which sodiumlauryl sulphate is predominant.

The composition comprising the compounds of formula (I) may preferably be provided in the form of an aqueous lotion, a gel, an emulsion, a cream, a foam or a paste for application to the skin, the teeth and/or the hair.

More preferably, it may be provided in the form of a shampoo, a shower gel, a toothpaste, a make-up removing milk or a lotion.

Depending on its intended use, the compositions of the present invention may also comprise fatty substances, especially natural or synthetic oils; thickening or gelling agents such as cellulose or its derivatives, acrylic polymers, alginates, gums, polyethylene glycols, bentonites and montmorillonites; humectants such as glycerine and triacetin; antioxidants; preservatives. Exemplary ingredients which may be used in the compositions of the present invention are set forth in U.S. Pat. No. 4,788,345, the disclosure of which is specifically incorporated herein by reference.

The invention is illustrated in greater detail in the following examples.

EXAMPLE 1

Preparation of N-2-ethylhexyloxycarbonyl-N-methyl-D-glucamine

In a reactor, 117 g (0.6 mol) of N-methyl-D-glucamine were dissolved in a mixture of 800 ml of water and 400 ml of tetrahydrofuran, and then 201.6 g (2.4 mol) of sodium hydrogen carbonate were dispersed therein.

While the temperature of the reaction mixture was maintained at 5° C., 115.6 g (0.6 mol) of 2-ethylhexyl chloroformate were added dropwise and allowed to react for three hours with stirring at 5° C., and overnight without stirring at room temperature. The reaction mixture was then filtered and concentrated; the pasty residue obtained was dissolved in 2 liters of acetone and then filtered after cooling to 5° C. The crystallized product recovered was dried.

105 g (50% yield) of N-2-ethyl-hexyloxycarbonyl-N-methyl-D-glucamine were obtained, whose melting point was 74° C.

EXAMPLE 2

Preparation of N-2-butyloctyloxycarbonyl-N-methyl-D-glucamine

The compound was prepared according to the same procedure as in Example 1, using:

78 g (0.4 mol) of N-methyl-D-glucamine 134.4 g (1.6 mol) of sodium bicarbonate 99.4 g (0.4 mol) of 2-butyloctyl chloroformate.

62 g of N-2-butyloctyloxycarbonyl-N-methyl-D-glucamine were obtained in the form of a white powder whose melting point was 77° C.

EXAMPLE 3

Preparation of N-2-ethylhexyloxycarbonyl-D-glucamine

The compound was prepared according to the same procedure as in Example 1, using:

23.50 g (0.13 mol) of D-glucamine 43.70 g of sodium bicarbonate 25.04 g (0.13 mol) of 2-ethylhexyl chloroformate.

N-2-ethylhexylcarbonyl-D-glucamine, whose melting point was 104° C., was obtained with a yield of 95%.

EXAMPLE 4

Preparation of N-2-butyloctyloxycarbonyl-D-glucamine

The compound was prepared according to the same procedure as in Example 1, using:

47.00 g (0.26 mol) of D-glucamine 84 g of sodium hydrogen carbonate, and 64.61 g (0.26 mol) of butyloctyl chloroformate.

N-2-butyloctyloxycarbonyl-D-glucamine, whose melting point was 100.7° C., was obtained with a yield of 45%.

EXAMPLE 5

Preparation of 2-N-(2-ethylhexyloxycarbonyl)-amino-1-ethanol

The compound was prepared according to the same procedure as in Example 1, using:

21.35 g (0.35 mol) of aminoethanol, 67 g of sodium bicarbonate, and 38.50 g (0.2 mol) of 2-ethylhexyl chloroformate.

After filtration of the salt formed, the mixture was concentrated under vacuum, and the compound was obtained in the form of a colourless oil, with a yield of 98%.

EXAMPLE 6

Preparation of 2-N-(2-butyloctyloxycarbonyl)-amino-1-ethanol

The compound was prepared according to the same procedure as in Example 1, using:

18.3 g (0.3 mol) of aminoethanol, 67.2 g of sodium bicarbonate, and 49.7 g (0.2 mol) of 2-butyloctyl chloroformate.

After filtration of the salt formed, the mixture was concentrated under vacuum, and the desired compound was obtained in the form of a colourless oil, with a yield of 99%.

EXAMPLE 7

Preparation of 2-N-(2-ethylhexyloxycarbonyl)-amino-2-hydroxymethyl-1,3-propanediol In a reactor, 30 g of tris(hydroxymethyl)-aminomethane were dissolved in a mixture of 125 ml of water and 170 ml of tetrahydrofuran, and then 84 g of sodium hydrogen carbonate were dispersed therein.

While the temperature of the reaction mixture was maintained at 50° C., 62 g of 2-ethylhexyl chloroformate were added dropwise and allowed to react for 3 hours with stirring at 5° C., and overnight without stirring at room temperature.

The reaction mixture was then filtered and concentrated; the pasty residue obtained was dissolved in 800 ml of acetonitrile and then heated, with stirring, at 40° C. for 1 h. The mixture was then filtered and then concentrated. The residue was purified by chromatography on a silica column in dichloromethane.

14 g (20% yield) of 2-N-(2-ethylhexyloxy-carbonyl) amino-2-hydroxymethyl-1,3-propanediol were obtained in the form of a white powder whose melting point was 64° C.

EXAMPLE 8

Preparation of 2-N-(2-butyloctyloxycarbonyl)-amino-2-hydroxymethyl-1,3-propanediol The compound was prepared according to the same procedure as in Example 7, using:

30 g of tris(hydroxymethyl)aminomethane 84 g of sodium hydrogen carbonate, and 62 g of 2-butyloctyl chloroformate.

The crude product was recrystallized from boiling ethanol.

22 g (55% yield) of 2-N-(2-butyloctyloxycarbonyl) amino-2-hydroxymethyl-1,3-propanediol were obtained in the form of a white powder, whose melting point was 67° C.

EXAMPLE 9

Preparation of 3-N-(2-ethylhexyloxycarbonyl)-amino-1,2-propanediol

In a reactor, 22.8 g of 3-amino-1,2-propanediol were dissolved in a mixture of 120 ml of water and 180 ml of tetrahydrofuran, and then 84 g of sodium hydrogen carbonate were dispersed therein.

While the temperature of the reaction mixture was maintained at 5° C., 48 g of 2-ethylhexyl chloroformate were added dropwise and then allowed to react for 3 hours with stirring at 5° C. and overnight without stirring at room temperature.

The reaction mixture was then filtered and concentrated; the pasty residue obtained was dissolved in 800 ml of acetone and then heated, with stirring, at 40° C. for 1 h. The mixture was then filtered and then concentrated.

60 g (97% yield) of 3-N-(2-ethylhexyloxycarbonyl) amino-1,2-propanediol were obtained in the form of a translucent oil.

EXAMPLE 10

Preparation of 3-N-(2-butyloctyloxycarbonyl)-amino-1,2-propanediol

The compound was prepared according to the same procedure as in Example 9, using:

22.8 g of 3-amino-1,2-propanediol 84 g of sodium hydrogen carbonate, and 62 g of 2-butyloctyl chloroformate.

74 g (97% yield) of 3-N-(2-butyloctyloxycarbonyl) amino-1,2-propanediol were obtained in the form of a translucent oil.

EXAMPLE 11

The plateau surface tension (γ plateau) and the critical micelle concentration (CMC) for N-2-ethylhexyloxycarbonyl-N-methyl-D-glucamine, a compound according to the invention, prepared in Example 1, and N-octanoyl-N-methyl-D-glucamine, sold under the name MEGA 8 by DOJINDO, a surfactant marketed especially in the cosmetic field, were compared.

The plateau surface tension and the CMC were deduced by measuring the static surface tension with the aid of a DU NOUY type ring tensiometer.

The following results were obtained:

|  | γ plateau (dyn/cm or mN/m) | CMC (mol/l) |
|---|---|---|
| Compound according to the invention | 26.5 | 0.011 |
| MEGA 8 | 39 | 0.052 |

It was thus observed that the surface tension of the compound of formula (I) was considerably less than that of the compound of the prior state of the art.

The compound according to the invention thus had surfactant properties superior to those of the compound of the prior state of the art.

It was also observed that the CMC of the compound of formula (I) was about 5 times lower than that of the compound of the prior state of the art, hence the usefulness of the compounds according to the invention which possess good surfactant properties even at a low concentration.

EXAMPLE 12

The skin behaviour of two compounds as surfactants, was compared:

sodiumlauryl sulphate (or NaLS), a customary surfactant, and

N-2-ethylhexyloxycarbonyl-N-methyl-D-glucamine, a compound according to the invention.

The comparison was made by means of the test described in "An in vitro method for evaluation of the irritancy of anionic surfactants" by Anavkar et al., published in JAOCS, volume 66, No. 9 (1989), pp. 1386–1389.

The principle of this test consists in determining the capacity, for the compounds considered, to extract a dye present inside a protein mass.

A protein matrix (gelatin gel) containing a specific dye (CBB or Comassie Brilliant Blue) was prepared. A solution of the considered compound was poured over the gel obtained and stirred at 105 revolutions/minute, at 20° C. for 30 minutes. The quantity of dye extracted was then measured by spectrophotometry at 590 nm.

This quantity was proportional to the irritant character of the surfactant for the support to which it was applied (skin, scalp and the like).

Thus, the lower the measured absorbance, the better the skin behaviour of the compound tested.

The following results were obtained:

| Compound considered | Absorbance at 590 nm |
|---|---|
| Aqueous solution containing 1% by weight of NaLS | 2.459 |
| Aqueous solution containing 1% by weight of the compound according to the invention | 0.552 |
| Aqueous solution containing 1% by weight of NaLS and 1% by weight of the compound according to the invention | 0.261 |

It can thus be considered that the compound according to the invention was a lot less irritating for the skin than a customary surfactant, NaLS.

Furthermore, the combination of the compound according to the invention with sodiumlauryl sulphate made it possible to reduce the aggressiveness of the latter.

EXAMPLE 13

A toothpaste having the following composition was prepared:

| | |
|---|---|
| precipitated amorphous silica | 20 g |
| titanium dioxide | 0.5 g |
| carboxymethyl cellulose | 1.4 g |
| sorbitol in aqueous solution containing 70% of active ingredient | 32 g |
| sodiumlauryl sulphate (93% of active ingredient) | 1 g |
| N-2-ethylhexyloxycarbonyl-N-methyl-D-glucamine | 1 g |

| | |
|---|---|
| sodium fluoride | 0.11 g |
| sodium monofluorophosphate | 0.38 g |
| sweetener, preservative and flavouring | qs |
| water | qs to 100 g |

EXAMPLE 14

A toothpaste having the following composition was prepared:

| | |
|---|---|
| precipitated amorphous silica | 20 g |
| titanium dioxide | 0.5 g |
| carboxymethyl cellulose | 1.4 g |
| sorbitol in aqueous solution containing 70% of active ingredient | 32 g |
| N-2-ethylhexyloxycarbonyl-N-methyl-D-glucamine | 1 g |
| sodium fluoride | 0.11 g |
| sodium monofluorophosphate | 0.38 g |
| sweetener, preservative and flavouring | qs |
| water | qs to 100 g |

EXAMPLE 15

A shower gel having the following composition was prepared:

| | |
|---|---|
| triethanolamine lauryl sulphate (40% of active ingredient | 30 g |
| cocoyl betaine (32% of active ingredient) | 10 g |
| sodiumlauryl sulphate (93% of active ingredient) | 5.4 g |
| N-2-ethylhexyloxycarbonyl-N-methyl-D-glucamine | 5 g |
| preservative, perfume, colorant | qs |
| NaOH or HCl | qs pH 7.2 |
| water | qs 100 g |

It is believed that such a shower gel will have good cosmetic properties.

EXAMPLE 16

A shower gel having the following composition was prepared:

| | |
|---|---|
| triethanolamine lauryl sulphate (40% of active ingredient | 30 g |
| cocoyl betaine (32% of active ingredient) | 10 g |
| N-2-ethylhexyloxycarbonyl-N-methyl-D-glucamine | 5 g |
| preservative, perfume, colorant | qs |
| NaOH or HCl | qs pH 7.2 |
| water | qs 100 g |

It is believed that such a shower gel will have good cosmetic properties.

EXAMPLE 17

A make-up removing milk having the following composition was prepared:

| | |
|---|---|
| isopropyl palmitate | 5 g. |
| carboxyvinyl copolymer (Pemulen TR2 from Goodrich) | 0.1 g |
| N-2-ethylhexyloxycarbonyl-N-methyl-D-glucamine | 3 g |
| NaOH | 0.02 g |
| preservative, perfume | qs |
| water | qs 100 g |

It is believed that such a make-up removing milk will have good cosmetic properties.

EXAMPLE 18

A gentle detergent lotion having the following composition was prepared:

| | |
|---|---|
| N-2-ethylhexyloxycarbonyl-N-methyl-D-glucamine | 3 g |
| sorbitan laurate (20 EO) | 2 g |
| xanthan gum | 0.15 g |
| 1,3-butylene glycol | 4 g |
| preservative, perfume | qs |
| water | qs 100 g |

It is believed that such a detergent lotion will be not very irritating for the skin.

What is claimed is:

1. A method of providing surfactant properties to a cosmetic or pharmaceutical composition, said method comprising using in said cosmetic or pharmaceutical composition a compound of formula (I):

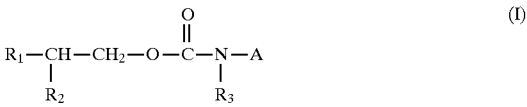

in which:

$R_1$ represents a linear or branched, saturated or unsaturated alkyl radical having 4 to 6 carbon atoms, $R_2$ represents a linear or branched, saturated or unsaturated alkyl radical having 2 to 4 carbon atoms, $R_3$ represents a hydrogen atom or a linear or branched, saturated or unsaturated alkyl radical having 1 to 6 carbon atoms, and A represents a radical of the formula:

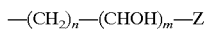

in which n is an integer equal to 0 or 1, m is an integer ranging from 0 to 4, and Z is a hydroxylated alkyl radical having from 1 to 4 carbon atoms, wherein said compound of formula (I) provides surfactant properties to said cosmetic or pharmaceutical composition.

2. The method according to claim 1, wherein in said compound of formula (I), Z represents:

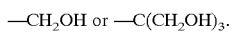

3. The method according to claim 1, wherein the compound of formula (I) is:
N-2-ethylhexyloxycarbonyl-N-methyl-D-glucamine,
N-2-butyloctyloxycarbonyl-N-methyl-D-glucamine,
N-2-ethylhexyloxycarbonyl-D-glucamine,
N-2-butyloctyloxycarbonyl-D-glucamine,
2-N-(2-ethylhexyloxycarbonyl)amino-2-hydroxymethyl-1,3-propanediol, 2-N-(2-butyloctyloxycarbonyl)amino-2-hydroxymethyl-1,
3-propanediol,
2-N-(2-ethylhexyloxycarbonyl)amino-1-ethanol,
2-N-(2-butyloctyloxycarbonyl)amino-1-ethanol,
3-N-(2-ethylhexyloxycarbonyl)amino-2-hydroxymethyl-1,
3-propanediol, or
3-N-(2-butyloctyloxycarbonyl)amino-2-hydroxymethyl-1,
3-propanediol.

4. The method according to claim 1, wherein the compound of formula (I) is present in said cosmetic or pharmaceutical composition in a concentration ranging from 0.1 to 10% by weight relative to the total weight of the composition.

5. The method according to claim 4, wherein the compound of formula (I) is present in said cosmetic or pharmaceutical composition in a concentration ranging from 0.5 to 5% by weight relative to the total weight of the composition.

6. The method according to claim 1, further comprising an additional surfactant other than said compound of formula (I).

7. The method according to claim 6, wherein said additional surfactant is sodium lauryl sulphate or sodium lauryl ether sulphate.

8. The method according to claim 7, wherein said additional surfactant is sodium lauryl sulphate.

9. The method according to claim 1, wherein said cosmetic or pharmaceutical composition is in the form of an aqueous lotion, a gel, an emulsion, a cream, a foam or a paste for application to the skin, the teeth or the hair.

10. The method according to claim 1, wherein said cosmetic or pharmaceutical composition is in the form of a shampoo, a shower gel, a toothpaste, a make-up removing milk, or a lotion.

11. The method according to claim 6, wherein said compound of formula (I) is N-2-(ethylhexyloxycarbonyl)-N-methyl-D-glucamine and said additional surfactant is sodium lauryl sulphate.

12. The method according to claim 11, wherein said N-2-(ethylhexyloxycarbonyl)-N-methyl-D-glucamine and said sodium lauryl sulphate are present in a 1:1 ratio.

13. The method according to claim 11, wherein said N-2-(ethylhexyloxycarbonyl)-N-methyl-D-glucamine is present in said cosmetic or pharmaceutical composition in an amount less than the amount of said sodium lauryl sulphate.

* * * * *